US005545821A

United States Patent [19]
Wong et al.

[11] Patent Number: 5,545,821
[45] Date of Patent: *Aug. 13, 1996

[54] PRODUCTION OF IMPROVED RAPESEED EXHIBITING A REDUCED SATURATED FATTY ACID CONTENT

[75] Inventors: Raymond S. C. Wong, Kowloon, Hong Kong; Ian Grant, Ontario, Canada; Jayantilal D. Patel, Ontario, Canada; Jeff P. K. Parker, Ontario, Canada; Eric B. Swanson, Ontario, Canada

[73] Assignee: Pioneer Hi-Bred International, Inc., Des Moines, Iowa

[ * ] Notice: The term of this patent shall not extend beyond the expiration date of Pat. No. 5,387,758.

[21] Appl. No.: 360,580

[22] Filed: Dec. 21, 1994

Related U.S. Application Data

[63] Continuation of Ser. No. 13,184, Jan. 29, 1993, Pat. No. 5,387,758, which is a continuation of Ser. No. 672,135, Mar. 21, 1991, abandoned, which is a continuation-in-part of Ser. No. 504,302, Apr. 4, 1990, abandoned.

[51] Int. Cl.$^6$ .............................. A01H 5/00; A01H 5/10; C12N 15/01; C12P 7/64
[52] U.S. Cl. .................... 800/230; 800/200; 800/255; 800/DIG. 17; 800/DIG. 69; 435/172.1; 435/134
[58] Field of Search .................................. 800/200, 230, 800/255, DIG. 17, DIG. 69; 435/172.1, 134

[56] References Cited

U.S. PATENT DOCUMENTS

| | | | |
|---|---|---|---|
| 4,517,763 | 5/1985 | Beversdorf et al. | 47/58 |
| 4,658,084 | 4/1987 | Beversdorf et al. | 800/200 |
| 4,658,085 | 4/1987 | Beversdorf et al. | 800/200 |
| 4,948,811 | 8/1990 | Spinner et al. | 514/560 |
| 5,387,758 | 2/1995 | Wang et al. | 800/230 |

FOREIGN PATENT DOCUMENTS

| | | |
|---|---|---|
| 0323753 | 7/1989 | European Pat. Off. . |
| 0326198 | 8/1989 | European Pat. Off. . |
| 1814440 | 7/1969 | Germany . |
| 1212118 | 11/1970 | United Kingdom . |
| WO92/03919 | 3/1992 | WIPO . |

OTHER PUBLICATIONS

"The Development of Improved Rapeseed Cultivars", B. R. Stefansson from High and Low Erucic Acid Rapeseed Oils, Chapter 6, edited by John K. G. Kramer, Frank D. Sauer, and Wallace J. Pigden, Academic Press Canada (1983).

"The Introduction of Low Erucic Acid Rapeseed Varieties Into Canadian Production", J. K. Daun from High and Low Erucic Acid Rapeseed Oils, Chapter 7, edited by John K. G. Kramer, Frank D. Sauer, and Wallace J. Pigden, Academic Press Canada (1983).

"Prospects for the Development of Rapeseed (*B. napus* L.) With Improved Linolenic and Linolenic Acid Content" by N. N. Roy and A. W. Tarr, *Plant Breeding*, vol. 98, pp. 89 to 96 (1987).

"Genetic Control of Fatty Acid Composition in Oilseed Crops", by R. K. Downey and D. G. Dorrell, *Proc. Flax Inst. U.S.A.*, vol. 47, No. 3, pp. 1 to 3.

Chapter 10, "Changes and Limitations of Breeding for Improved Polyenoic Fatty Acids Content in Rapeseed" by Gerhard Röbblen from Biotechnology for the Oils and Fats Industry, edited by Colin Ratledge, Peter Dawson, and James Rattray, American Oil Chemists' Society, pp. 97–105 (1984).

J. K. Daun et al., *J. Amer. Oil Chem. Soc.*, 60: pp. 1751–1754 (1953).

Chapter 8, "Rapeseed Crushing and Extraction" by D. H. C. Beach from High and Low Erucic Acid Rapeseed Oils edited by John K. G. Kramer, Frank D. Sauer, and Wallace J. Pigden, Academic Press Canada, pp. 181–195 (1983).

"Methods for Breeding for Oil Quality in Rape", R. K. Downey and B. L. Harvey reported in *Canadian Journal of Plant Science*, vol. 43, pp. 271–275 (1963).

"Relationships Between Major Fatty Acids of Oleiferous Species of Brassica", by Lutfur Rahmnan, *Indian J. Agric. Sci.*, vol. 48, No. 7, pp. 401–406 (Jul. 1978).

"Selektion auf Linol–und Linolensaurregehalt in Rapeseed Nach Mutagener Behandlung", by G. Rakow, *Z. Pflanzenzuchtg*, 69, pp. 62–82 (1973).

"Breeding for Improved $C_{18}$–Fatty Composition in Rapeseed"(Brassica napus L.), S. Pleines and W. Freidt, Fat. Sci. Technology, vol. 90(5), pp. 161–171 (1988).

(List continued on next page.)

Primary Examiner—David T. Fox
Attorney, Agent, or Firm—Burns, Doane, Swecker & Mathis

[57] ABSTRACT

Improved rape plants, seeds capable of forming the same, and a novel improved edible endogenous vegetable oil derived from the rapeseeds are provided. Such plants have the ability to yield an endogenous vegetable oil having an unusually low saturated fatty acid content. More specifically, the rape plants upon self-pollination are capable of forming rapeseeds which yield an improved vegetable oil following crushing and extraction having a saturated fatty acid content of no more than 4 percent by weight (preferably no more than 3.5 percent by weight and most preferably less than 3 percent by weight) in the form of stearic and palmitic acids based upon the total fatty acid content. A relatively low concentration of erucic acid (as described) also is exhibited in the endogenous oil. It has been found that the novel rape plants of the present invention can be formed by mutagenesis followed by selection as described. The endogenous vegetable oil produced by the improved rape plants of the present invention is particularly well suited for use as a vegetable oil (e.g., for use in a salad dressing, cooking applications, etc.). Accordingly, the present invention makes possible a further significant reduction in the already relatively low concentration of saturated fatty acid commonly present in quality vegetable oils derived from rapeseeds. In a preferred embodiment the plants additionally possess herbicide tolerance which facilitates their survival when unwanted plants which lack the reduced saturated fatty acid content are eliminated through the use of a herbicide.

33 Claims, No Drawings

OTHER PUBLICATIONS

"Genetical and Physiological Investigations on Mutants for Polyenoic Fatty Acids in Rapeseed, *Brassica napus* L. ", by G. Röbbelen and A. Nitsch, *Z. Pflanzenzüchtg.*, 75, pp. 93 to 105 (1975).

"Isolation, expression and phylogenetic inheritance of acetolactate synthase gene from *Brassica napus*", P. A. Wiersma et al., *Mol. Gen. Genet.*, 219, pp. 413–420 (1989).

*Plant Cell Reports*, 6:94–97 (1987), Eric Swanson et al.

"The Characterization of Herbicide Tolerant Plants in *Brassica napus* L. After In Vitro Selection of Microspores and Protoplasts" by Eric B. Swanson et al., *Plant Cell Reports*, (1988) 7:83–87.

"Dupont and AGS Transfer Resistance to Sulfonylurea Herbicides", *Agricultural Genetics Report*, vol. 6, No. 2, Apr.; 1987.

"Recurrent Selection for Modified Polyenoic Fatty Acid Composition in Rapeseed (*Brassica napus* L.)", S. Pleines, R. Marguard, and W. Freidt, 7th International Rapeseed Congress, pp. 23 (abstract) (1987).

"Recurrent Selection for Modified Polyenoic Fatty Acid Composition in Rapeseed (*Brassica napus* L.)" S. Pleines, R. Marguard, and W. Freidt, 7th International Rapeseed Congress, pp. 140–to 145 (May 11–14, (1987).

"Genetic Control of Linolenic Acid Concentration in Seed Oil of Rapeseed (*Brassica napus* L.)", S. Pleines and W. Freidt, *Theor. Appl. Genet.* (1989) 78:793–797.

"Breeding Rapeseed for Oil and Meal Quality", by R. K. Downey, B. M. Craig, and C. G. Youngs, Journal of the American Oil Chemists' Society, vol. 46, pp. 121 to 123 (Mar. 1969).

"Rapeseed" by Appelquist and Ohlson, published by Elsivier (1972), pp. 117 to 122.

"Rape and Mustard Breeding for Oil Quality" by V. I. Shopta of the U.S.S.R., Proceedings International Rapeseed Conference, Pornan, Poland, pp. 560 to 565 (May 1987).

"Untersuchungen über die genotypische Variation des C18–Fettsäuremusters bei Raps (Brassica napus L.) und Möglichkeiten ihrer züchterischen Nutzung". Inaugural Dissertation of Stephen Pleines to obtain the degree of Dr. in the field of agricultural sciences at the Justus–Liebig University Giessen. English translation of the above entitled Investigation of the Genotypical Variation of the C18–Fatty Acid Pattern in Rape (Brassica napus L.) and Posssible Applications to Breeding. Published Feb. 10, 1989).

"Breeding for Improved Fatty Acid Composition in Rapeseed", by Roland Jönsson and Christer Persson, *Proc. 6th Int. Rapeseed Conference*, pp. 311 to 314 (1983).

"Quality Breeding in Rapeseed –Sovalof 1886–1986" by Roland Jönsson and Bengt Uppström, pp. 173 to 183 (1986).

"Microspore Mutagenesis and Selection: Canola Plants With Field Tolerance to the Imidazolinones", by Eric B. Swanson et al., *Theor. Appl. Genetics* 78, pp. 525–530 (1989).

Plaines et al. 1988. Fat Sci. Technol. 90(5): 161–171.

Rahman, L. 1978. Indian J. Agric. Sci. 48(7): 401–406.

Downey et al. 1969. J. Am. Oil Chem. Soc. 46: 121–123.

PRODUCTION OF IMPROVED RAPESEED EXHIBITING A REDUCED SATURATED FATTY ACID CONTENT

CROSS-REFERENCE TO RELATED APPLICATION

This application is a continuation, of application Ser. No. 08/013,184, filed Jan. 29, 1993 (now U.S. Pat. No. 5,387,758, granted Feb. 7, 1995) which is a continuation of application Ser. No. 07/672,135, filed Mar. 21, 1991 (now abandoned) which is a Continuation-In-Part application of U.S. Ser. No. 07/504,302 filed Apr. 4, 1990 (now abandoned).

BACKGROUND OF THE INVENTION

Rape (.i.e., *Brassica napus* and *Brassica campestris*) is being grown as an increasingly important oilseed crop in many parts of the world. As a source of vegetable oil, it presently ranks behind only soybeans and palm and is virtually tied with sunflower for the number three position of commercial importance. The oil is used as both a salad oil and a cooking oil throughout the world.

In its original form rapeseed oil was found to have deleterious effects on human health due to its relatively high level of erucic acid which commonly is present in native cultivars in concentrations of 30 to 50 percent by weight based upon the total fatty acid content. In the past plant scientists identified a germplasm source of low erucic acid rapeseed oil and began incorporating this trait into commercial cultivars. See, Chapter 6 entitled "The Development of Improved Rapeseed Cultivars" by B. R. Stefansson from "High and Low Erucic Acid Rapeseed Oils" edited by John K. G. Kramer, Frank D. Sauer, and Wallace J. Pigden, Academic Press Canada (1983).

In Canada, plant scientists focused their efforts on creating so-called "double-low" varieties which were low in erucic acid in the oil and low in glucosinolates in the solid meal remaining after oil extraction (i.e., an erucic acid content of less than 2 percent by weight based upon the total fatty acid content, and a glucosinolate content of less than 30 micromoles per gram of the oil-free meal). These higher quality forms of rape developed in Canada are known as canola.

In contrast, European scientists worked to achieve only "single-low" types which were low in erucic acid, but did not attempt to improve the quality of the solid meal which retained a glucosinolate content of about 100 micromoles per gram of oil-free meal. The result of this major change in the fatty acid composition of rapeseed oil was to create an entirely new oil profile which often contained approximately 6 percent or more by weight of saturated fatty acid in the form of stearic acid and palmitic acid based upon the total fatty acid content. Since the overall percentage of oil in the seed did not change appreciably when the new low erucic cultivars were developed, it appeared that the erucic acid oil component had simply been redirected into other fatty acids within the oil. See, Chapter 7 entitled "The Introduction of Low Erucic Acid Rapeseed Varieties Into Canadian Production" by J. K. Daun from the previously identified Academic Press Canada (1983) publication, "Prospects for the Development of Rapeseed (*B. napus* L.) With Improved Linoleic and Linolenic Acid Content" by N. N. Roy and A. W. Tarr, *Plant Breeding*, Vol. 98, Pages 89 to 96 (1987), and "Genetic Control of Fatty Acid Composition in Oilseed Crops" by R. K. Downey and D. G. Dorrell, *Proc. Flax Inst. U.S.A.*, Vol. 47, No. 3, pages 1 to 3. In the latter article it was speculated at Page 2, Table 4, with respect to *Brassica napus* and *Brassica campestris* in general that a minimum palmitic acid content may be 2.8 percent and a minimum stearic acid content may be 0.4 percent. These values have not heretofore been present in rapeseed having a low erucic acid content in the vegetable oil.

European Patent Application 0 323 753 discloses the production of rapeseed exhibiting an enhanced oleic acid content.

European Patent Application 0 326 198 and U.S. Pat. No. 4,948,811 make reference to the advantages of having a salad/cooking oil which has a saturates concentration of less than about 3 percent. In the working examples the oil is formed by chemical reaction or by physical separation of saturates. Passing reference is made to "genetic engineering" at Col. 3, line 58 of the United States Patent. There is no enabling disclosure of how canola (or any other oilseed plant) could be modified to provide an improved edible endogenous vegetable oil as presently disclosed.

At the present time, canola oil is being marketed by Procter & Gamble under the Puritan trademark. Such vegetable oil typically is free of cholesterol, and the fatty acids present in it consist of approximately 6 percent saturated fatty acids in the form of stearic and palmitic acids, approximately 22 percent by weight linoleic acid which contains two double bonds per molecule of 18 carbon atoms, approximately 10 percent by weight alpha-linolenic acid which contains three double bonds per molecule of 18 carbon atoms, approximately 62 percent by weight oleic acid which contains a single double bond per molecule of 18 carbon atoms, and less than one percent by weight erucic acid which contains a single double bond per molecule of 22 carbon atoms.

Over the years scientists have attempted to improve the fatty acids profile for canola oil. See, for instance, Chapter 10 by Gerhard Röbbelen entitled "Changes and Limitations of Breeding for Improved Polyenic Fatty Acids Content in Rapeseed" from "Biotechnology for the Oils and Fats Industry" edited by Colin Ratledge, Peter Dawson, and James Rattray, American Oil Chemists' Society (1984).

In recent years studies have associated the increased intake of saturated fatty acids having no double bonds, such as stearic and palmitic acids, with the presence of increased serum cholesterol in the blood. The increased serum cholesterol in turn has been associated with increased risk for coronary heart disease. Presently available canola oil is recognized to be a superior dietary oil because it contains the lowest saturated fat level (e.g., 6 percent by weight in the form of stearic acid and palmitic acid based upon the total fatty acid content) of any edible vegetable oil. Nevertheless, canola varieties which exhibit even lesser quantities of saturated fatty acids in the oil have not been available to the canola grower in spite of the recognized advantages of limiting saturated fatty acids in the diet.

As reported in U.S. Pat. Nos. 4,517,763; 4,658,084; and 4,658,085; and the publications identified therein, hybridization processes suitable for the production of rapeseed are known wherein herbicide tolerance is utilized.

It is an object of the present invention to provide a substantially uniform assemblage of improved rapeseeds which yield edible vegetable oil having a substantially reduced saturated fatty acid content.

It is an object of the present invention to provide a substantially uniform assemblage of improved rapeseeds which yield a vegetable oil having a substantially reduced saturated fatty acid content in combination with other desirable characteristics.

It is an object of the present invention to provide a substantially uniform assemblage of improved rapeseeds which yield a vegetable oil having a substantially reduced saturated fatty acid content with no substantial reduction in the alpha-linolenic acid content normally exhibited by canola.

It is an object of the present invention to provide a substantially uniform stand of rape plants which are capable upon self-pollination of forming rapeseeds which yield a vegetable oil which possesses a substantially reduced saturated fatty acid content.

It is an object of the present invention to provide a substantially uniform stand of rape plants capable upon self-pollination of forming rapeseeds which yield a vegetable oil which possesses a substantially reduced saturated fatty acid content in combination with other desirable characteristics.

It is another object of the present invention to provide a substantially uniform stand of rape plants which in a preferred embodiment exhibit herbicide tolerance and upon self-pollination form rapeseeds which yield a vegetable oil possessing a substantially reduced fatty acid content thereby making possible the elimination of unwanted contaminant plants (e.g., those possessing the usual elevated saturated fatty acid content) through the use of a herbicide.

It is another object of the present invention to provide an improved vegetable oil derived from rapeseeds.

It is a further object of the present invention to provide a method for lowering the saturated fatty acid content of rapeseeds.

These and other objects and advantages of the invention will be apparent to those skilled in the art from a reading of the following description and appended claims.

SUMMARY OF THE INVENTION

A substantially homogeneous assemblage of mature rapeseeds is provided which is capable of yielding an improved edible endogenous vegetable oil of reduced saturated fatty acid content having (1) an oil which exhibits following crushing and extraction an unusually low saturated fatty acid content in the vegetable oil of no more than 4 percent by weight in the form of stearic acid and palmitic acids based upon the total fatty acid content wherein the saturated fatty acid content is controlled by genetic means for the expression of such trait, and (2) an oil which exhibits following crushing and extraction a erucic acid content in the vegetable oil of no more than 2 percent by weight based on the total fatty acid content.

A substantially uniform stand of rape plants is provided which upon self-pollination are capable of forming rapeseeds which yield an improved edible endogenous vegetable oil, said rapeseeds having (1) an oil which exhibits following crushing and extraction an unusually low saturated fatty acid content in the vegetable oil of no more than 4 percent by weight in the form of stearic and palmitic acids based upon the total fatty acid content wherein the saturated fatty acid content is controlled by genetic means for the expression of such trait, and (2) an oil which exhibits following crushing and extraction a erucic acid content in the vegetable oil of no more than 2 percent by weight based on the total fatty acid content.

An improved edible endogenous vegetable oil extracted from rapeseeds of reduced saturated fatty acid content is provided, the rapeseeds having (1) an oil which exhibits following crushing and extraction an unusually low saturated fatty acid content of no more than 4 percent by weight in the form of stearic and palmitic acids based upon the total fatty acid content, and (2) an oil which exhibits following crushing and extraction a erucic acid content of no more than 2 percent by weight based on the total fatty acid content.

A method for lowering the saturated fatty acid content of rapeseeds comprising:

(a) subjecting in at least one generation cells derived from a rapeseed plant which initially yields an endogenous vegetable oil having a saturated fatty acid content of at least 5 percent by weight in the form of stearic and palmitic acids based upon the total fatty acid content to a technique selected from the group consisting of contact with a chemical mutagen, gamma irradiation, and a combination of the foregoing, in order to induce mutagenesis with respect to a reduced production of saturated fatty acids, (b) regenerating said cells to produce a rape plant and to form rapeseeds in at least one generation subsequent to that of step (a), (c) selecting a rapeseed produced in step (b) which yields a vegetable oil having an endogenous saturated fatty acid content of no more than 4 percent by weight in the form of stearic and palmitic acids based upon the total fatty acid content, and (d) producing rape plants in a subsequent generation derived from the selection of step (c) having substantial genetic homogeneity and forming rapeseeds thereon which contain an endogenous oil which exhibits following crushing and extraction an unusually low saturated fatty acid content of no more than 4 percent by weight based upon the total fatty acid content wherein the saturated fatty acid content is controlled by genetic means for the expression of such trait resulting from such mutagenesis.

DESCRIPTION OF PREFERRED EMBODIMENTS

Heretofore available rapeseed plants of low erucic acid content, whether *Brassica napus, Brassica campestris,* or *Brassica juncea,* have formed rapeseeds which possess a saturated fatty acid content in the vegetable oil in the form of stearic acid and palmitic acid on the order 6 percent or more by weight based upon the total fatty acid content. Accordingly, heretofore a need has persisted for improved canola varieties which exhibit a significantly reduced saturated fatty acid content. For the purposes of the present invention the saturated fatty acid content of a given rapeseed is determined by a standard procedure wherein the oil is removed from the rapeseeds by crushing the seeds and is extracted as fatty acid methyl esters following reaction with methanol and sodium hydroxide. Next the resulting ester is analyzed for fatty acid content by gas liquid chromatography using a capillary column which allows separation on the basis of the degree of unsaturation and chain length. This analysis procedure is described in the work of J. K. Daun et al, *J. Amer. Oil Chem. Soc.* 60:1751–1754 (1983) which is herein incorporated by reference.

In accordance with the concept of the present invention one preferably selects plant cells capable of regeneration (e.g., seeds, microspores, ovules, pollen, vegetative parts) from any of the canola varieties which are recognized to have superior agronomic characteristics. Such plant cells may be derived from *Brassica napus* or *Brassica campestris* plants. The *Brassica napus* plants may be of either the summer or winter types. The plant cells derived from a rapeseed plant which initially yields a vegetable oil having a saturated fatty acid content of at least 5 percent by weight (e.g., at least 5 or 6 percent by weight) in the form of stearic and palmitic acids based upon the total fatty acid content next are subjected in at least one generation to mutagenesis, a rape plant is regenerated from the cells to produce a rape plant and to form rapeseed in at least one subsequent generation, rapeseed is selected having a saturated fatty acid content of no more than 4 percent by weight (e.g., 2.5 to 4 percent by weight) and preferably no more than 3.5 percent by weight (e.g., 2.5 to 3.5 percent by weight) in the form of stearic and palmitic acids based upon the total fatty acid content, and a rape plant is produced on the basis of this selection which forms rapeseeds containing an endogenous oil which exhibits following crushing and extraction an unusually low saturated fatty acid content of less than 4 percent by weight based upon the total fatty acid content. Such rape plants may be produced via self-pollination for a sufficient number of generations (e.g., 2 to 8 generations) to achieve substantial genetic homogeneity. Alternatively, the characteristics may be fixed through the generation of a new plant from a haploid microspore cell, causing the haploid to double, and producing a homozygous diploid plant in accordance with known techniques.

The mutagenesis preferably is carried out by subjecting the plant cells (e.g., a rapeseed) to a technique selected from the group consisting of contact with a chemical mutagen, gamma irradiation, and a combination of the foregoing, for a sufficient duration to accomplish the desired lowering of saturated fatty acid content via a genetic modification but insufficient to destroy the viability of the cells and their ability to be regenerated into a plant. The rapeseed preferably possesses a moisture content of approximately 5 to 6 percent by weight at the time of such mutagenesis. The desired mutagenesis may be accomplished by use of chemical means such as by contact with ethylmethylsulfonate, ethylnitrosourea, etc., and by the use of physical means such as x-ray, etc. The mutagenesis also may be carried out by gamma radiation, such as that supplied by a Cesium 137 source. The gamma radiation preferably is supplied to the plant cells (e.g., a rapeseed) in a dosage of approximately 60 to 200 Krad., and most preferably in a dosage of approximately 60 to 90 Krad. It should be understood that even when operating at radiation dosages within the ranges specified, some plant cells (e.g., rapeseeds) will lose their viability and must be discarded.

It will be appreciated that the mutagenesis treatment will result in a wide variety of genetic changes within the rape plants which are produced. Many of these changes will be deleterious to the viability of the resulting plant over an extended period of time. Some changes also will produce viable plants which possess deficient agronomic characteristics. Such off-types may be simply discarded. However, if desired plants which have undergone mutation with respect to reduced fatty acid production coupled with undesirable agronomic traits can be retained and used as breeding or source material from which plants having the targeted trait coupled with satisfactory agronomic characteristics are derived.

Following mutagenesis, rape plants are regenerated from the treated cells using known techniques. For instance, the resulting rapeseeds may be planted in accordance with conventional rape growing procedures and following self-pollination rapeseed is formed thereon. Alternatively, doubled haploid plantlets may be extracted to immediately form homogeneous plants. The planting of the treated rapeseed preferably is carried out in a greenhouse in which the pollination is carefully controlled and monitored. Additional rapeseed which is formed as a result of such self-pollination in the present or a subsequent generation is harvested and is subjected to analysis for saturated fatty acid content in the oil. Since *Brassica napus* and *Brassica campestris* are dicotyledons, the analysis for saturated fatty acid content can be carried out on a single outer cotyledon (i.e., halfseed), and the remaining halfseed can be retained for possible future germination if the saturated fatty acid content is found to be favorable as a result of the mutagenesis. The rapeseeds can be carefully separated into two halfseeds using known techniques.

When a mature halfseed is found to possess a reduced saturated fatty acid content, it is selected and is retained. The desired saturated fatty acid content in the form of stearic and palmitic acids in the vegetable oil may range from 2.5 to 4 percent by weight, and preferably from 2.5 to 3.5 percent by weight based upon the total fatty acid content.

The other halfseed, which will be genetically the same as the halfseed which was subjected to halfseed analysis, can next be caused to germinate and a rape plant is formed from the same and allowed to undergo self-pollination. Such planting of the halfseed preferably also is carried out in a greenhouse in which the pollination is carefully controlled and monitored. The resulting rapeseed is harvested, planted, and is self-pollinated for a sufficient number of generations to achieve substantial genetic homogeneity. The genetic stabilization of the rape plant material enables the creation of plants having a reasonably predictable genotype which can be used as breeding or source material for the production of other improved rape varieties, as a finished variety for use by the rapeseed grower, or as a parent in the production of hybrid rapeseed with the reduced saturated fatty acid content being transferred to the progeny.

The resulting rapeseeds also are selected so that they possess the erucic acid content of canola (i.e., no more than 2 percent by weight based on the total fatty acid content). The erucic acid content in the endogenous oil following crushing and extraction preferably is less than 0.1 percent by weight (e.g., less than 0.05 percent by weight) based upon the total fatty acid content. Preferably, rapeseeds also are selected to possess an alpha-linolenic acid content of approximately 8 to 15 percent by weight based upon the total fatty acid content, and a glucosinolate content in the solid component following crushing and extraction of the oil of less than 100 micromoles per gram (preferably less than 30 micromoles per gram). The glucosinolate content may be any one or a mixture of 3-butenyl glucosinolate, 4-pentenyl glucosinolate, 2-hydroxy-3-butenyl glucosinolate, and 2-hydroxy-4-pentenyl glucosinolate. The gluconsinolate determination preferably is made on the air-dry-oil-free solid as measured by the gas liquid chromatograph method of the Canadian Grain Commission. The alpha-linolenic acid, erucic acid and glucosinolate levels commonly are made possible by selecting starting materials which already possess highly desirable levels of these components, and by making selections which retain these values following mutagenesis.

The desired traits described herein (e.g., unusually low saturated fatty acid content) once established can be readily transferred into other plants within the same *Brassica napus* or *Brassica campestris* species by conventional plant breeding techniques involving cross-pollination and selection of the progeny. It has been demonstrated that the characteristics are highly heritable, can be transmitted to their progeny, and can be recovered in segregating progeny in subsequent generations following crossing. Also, once established the desired traits can be transferred between the *napus* and *campestris* species using the same conventional plant breeding techniques involving pollen transfer and selection. The transfer of other traits, such as low erucic acid content, between the *napus* and *campestris* species by standard plant breeding techniques is already well documented in the technical literature. See, for instance, *Brassica crops and Wild Allies Biology and Breeding*, edited by S. Tsunada, K. Hinata, and Gomez Campo, Japan Scientific Press, Tokyo (1980). As an example of the transfer of the desired traits described herein (e.g., unusually low saturated fatty acid content) from *napus* to *campestrin*, one may select a commercially available *campestris* variety such as Tobin, Horizon, or Colt and carry out an interspecific cross with an appropriate plant derived from a *napus* breeding line discussed hereafter (i.e., F32-38-172-X or D-98-49-176). Alternatively, other *napus* breeding lines may be reliably and independently developed when following the mutagenesis techniques described herein. The Tobin variety is available from Agriculture Canada, Saskatoon, Saskatchewan, and other distributors. The Horizon and Colt varieties are available from Bonis & Company Ltd. of Lindsay, Ontario, Canada. Following the interspecific cross, members of the $F_1$ generation are self-pollinated to produce $F_2$ seed. Selection for the desired traits (e.g, unusually low saturated fatty acid content) is then conducted on single $F_2$ seeds which are then backcrossed with the *campestris* parent through the number of generations required to obtain a euploid (n=10) *campestris* line exhibiting the desired traits (e.g., unusually low saturated fatty acid content).

In accordance with the concept of the present invention the rapeseeds possessing the specified combination of characteristics are multiplied to form a substantially uniform assemblage of such seeds (e.g., a bag of such seeds) which can be used to produce a substantially uniform stand of such rape plants. The rapeseeds present in such assemblage number at least 250 seeds, and the resulting substantially uniform stand of rape plants numbers at least 250 plants.

The improved vegetable oil of the present invention may be formed by simple extraction in a direct manner from the mature rapeseeds such as by crushing and extraction in accordance with known techniques. See, for example, Chapter 8 entitled "Rapeseed Crushing and Extraction" by D. H. C. Beach appearing in "High and Low Erucic Acid Rapeseed Oils," Academic Press Canada (1983) which is herein incorporated by reference. In a preferred embodiment the vegetable oil is present in a quantity convenient for commercial or domestic use (e.g., a quantity of at least one liter).

The theory whereby the mutagenesis has been found to be capable of lowering the saturated fatty acid content is considered to be complex and incapable of simple explanation. For instance, the mutagenesis may result in the enhancement of enzyme activity in a qualitative or quantitative manner leading to the desaturation of the carbon chains of the fatty acids. Alternatively, the mutagenesis may modify the oil biosynthesis pathway so as to otherwise minimize the presence of saturated fatty acids in the resulting vegetable oil.

In accordance with a preferred embodiment of the present invention herbicide tolerance additionally is genetically conferred to the plants of the present invention which are capable of yielding an improved edible endogenous vegetable oil of reduced saturated fatty acid content. When a hybrid is to be produced, the herbicide tolerance is possessed by each of the parent plants (e.g, a self-incompatible seed parent and a restorer pollinator) as well as the resulting $F_1$ hybrid. Alternatively, the herbicide tolerance is present in a pureline variety. Genetic means for the required herbicide tolerance have heretofore been reported in the literature. However, such herbicide tolerance is highly atypical for rape cultivars which currently are being grown for rapeseed production. Such unusually low saturated fatty acid content of the oil and the herbicide tolerance can with appropriate selection coexist in the rape plant without interference with the expression of either trait. Also, a suitable herbicide can be applied at an effective concentration to eliminate rape plants which lack the herbicide tolerance without yield reduction in the surviving plants or an alteration of the desired unusually low saturated fatty acid content of the surviving rape plants.

When either pureline or hybrid rape cultivars of the present invention are grown one must be mindful of the possibility of the introduction of contamination wherein the saturated fatty acid content is elevated above the specified level. Such contamination generally is phenotypically invisible and may be difficult to detect particularly when large volumes of rapeseed are subjected to random analysis. It is impossible to physically separate and discard rapeseeds which possess the usual saturated fatty acid content in the oil. The source of such contamination may arise from pollen produced by conventional rape cultivars being grown in the same general area, volunteer rape plants, or wild mustard plants which appear as weeds in or near the area where the rape plants of the present invention are grown. Even a relatively low level of contamination resulting from extraneous pollen can serve to deleteriously alter the desired level of saturated fatty acids in the endogenous vegetable oil which is produced following crushing and extraction. In the absence of the added assurance offered by such herbicide tolerance it is essential during the production of the planting seed and the production of the rapeseed crop to maintain strict and ample isolation and the strict elimination of possible potential extraneous pollinators in the field and nearby fallow areas so as to preclude any substantial risk of contamination.

Rape plants capable of producing pollen that contributes to an unwanted elevated saturated fatty acid content in the oil can be eliminated through the action of an effective concentration of a herbicide while retaining the viability of the rape plants of the present invention which are capable of yielding the improved edible endogenous oil of the present invention having a reduced saturated fatty acid content (as specified). Alternatively, rape plants which are capable of forming unwanted seeds having an elevated saturated fatty acid content can be selectively eliminated. Such herbicide can be applied at least one time during the production of the rape plants. For instance, the herbicide can be (1) applied to the soil prior to planting, (2) applied to the soil after planting and prior to germination, and/or (3) applied at the post-emergent stage. If desired, rape plants which possess the requisite herbicide tolerance can be grown in an area where the soil includes a residual herbicide which was applied during an earlier growing season. It has been found that an ideal post-emergent herbicide application can be accomplished by spraying the rape plants once they have formed approximately 4 to 5 leaves. It also is recommended that the herbicide be applied to fallow areas adjacent the planting area when the occurrence of wild mustard plants or rape plants derived from a previous year's crop are considered to be a potential source of unwanted pollen production. In a preferred embodiment all rape fields are sprayed with the herbicide at the post-emergent stage during the buildup of the parent lines as are the production fields in which the improved specialty oil crop of the present invention is produced. This helps to insure the production of the desired improved rapeseed crop on a highly reliable and consistent basis.

The herbicide can be introduced into the planting area in accordance with its customary application technique (i.e., time and mode of application) at a rate which is effective to destroy unwanted rape plants which are capable of yielding an endogenous oil of the usual elevated level of saturated fatty acid content while still enabling the rape plants of the present invention to carry on normal plant functions without any significant interruption. The optimum herbicide application rate may vary with the herbicide which is selected and can be determined by routine experimentation. The minimum herbicide application rate preferably is selected which will reliably achieve the desired result. The conventional application of a herbicide to eliminate unwanted wild mustard plants in the area is rendered unnecessary.

The herbicide utilized may be of varied chemical composition so long as it effectively destroys the unwanted plants and has no significant deleterious influence upon the plants of the present invention. In preferred embodiments the herbicide is of the sulfonylurea or imidazolinone types. For instance, chlorsulfuron commonly can be incorporated into the soil prior to planting or applied post-emergently at a rate of approximately 10 to 25 grams per hectare depending upon the soil type and climatic conditions. Such chlorsulfuron is commercially available from DuPont under the GLEAN trademark. An imidazolinone herbicide available from American Cyanamid under the PURSUIT trademark, AC263,499, <5-ethyl-2-(4-isopropyl-4-methyl-5-oxo-2-imidazolin-2-yl)nicotinic acid>, can be incorporated in the soil prior to planting or applied post-emergently at a rate of approximately 25 to 100 grams per hectare depending upon the soil type and climatic conditions. Alternatively, an imidazolinone herbicide available from American Cyanamid under the ASSERT trademark commonly can be applied post-emergently at a rate of approximately 500 to 1,000 grams per hectare depending upon the soil type and climatic conditions. Other herbicides may be similarly utilized so long as they satisfy the above prerequisites.

A genetic determinant for the herbicide tolerance once located can be readily transferred into other rape plants by conventional plant breeding techniques involving cross-pollination and selection of the progeny in the same manner the capability to form an endogenous oil of unusually low saturated fatty acid content is transferred. Commonly the required genetic determinant for herbicide tolerance is found to be controlled by a semidominant Mendelian gene which should be present in the homozygous state in order to achieve the requisite level of tolerance in rape. Once introduced such herbicide tolerance is fixed in a homogeneous state by continued self-pollination followed by selection and/or haploid production which results in a plant having a substantially uniform phenotype. In a preferred embodiment the requisite herbicide tolerance trait is not only present in the plants of the present invention but is closely linked to the genetic means for the production of the unusually low saturated fatty acid content of the endogenous oil (as described). This enables the more expeditious transfer of both traits into other rape cultivars since the selection procedure is simplified.

Suitable sources for genetically-controlled herbicide tolerance in rape previously have been reported in the literature such as:

(a) "The Characterization of Herbicide Tolerant Plants in *Brassica napus* L. After in Vitro Selection of Microspores and Protoplasts" by Eric B. Swanson, et al. appearing in *Plant Cell Reports* (1988) 7:83–87.

(b) "Microspore Mutagenesis and Selection: Canola Plants With Field Tolerance to the Imidazolinones" by E. B. Swanson, et al , *Theor. Appl. Genet.* (1989) 78:525–530.

(c) "Isolation, Expression and Phylogenetic Inheritance of an Acetolactate Synthase Gene From *Brassica napus*", by P. A. Wiersma et al. appearing in *Mol. Gen. Genet.* (1989) 219:413–420.

Alternatively, a genetic determinant for the required herbicide tolerance can be transferred to rape plants from other plant sources, such as tobacco, through the use of techniques which have been reported in the technical literature. See, for instance, "DuPont and AGS Transfer Resistance to Sulfonylurea Herbicides" appearing in *Agricultural Genetics Report*, Vol. 6, No. 2, April 1987.

Additionally, such herbicide tolerance can be imparted to the rape plants using a microspore-based selection process wherein embryos are generated from the microspores and are subjected to a herbicide under conditions wherein selection for herbicide tolerance is accomplished. Such procedure is fully described in U.S. Ser. Nos. 173,165, filed Mar. 25, 1988, and 426,298, filed Oct. 25, 1989 which are herein incorporated by reference. As discussed therein, a rape plant source having tolerance to PURSUIT and ASSERT imidazolinone herbicides has been designated PM-1 and has been deposited under the Budapest Treaty in the American Type Culture Collection, 12301 Parklawn Drive, Rockville, Md. 20852, U.S.A., under Accession No. 40683. Also, as discussed therein a rape plant source having tolerance to both chlorsulfuron and the PURSUIT and ASSERT imidazolinone herbicides has been designated PM-2 and likewise has been deposited under the Budapest Treaty at the same depository where it has been accorded Accession No. 40684. If desired the genetic determinants for herbicide tolerance of PM-1 and PM-2 can be combined into a single rape plant using known recombination techniques. These seed deposits will be made available upon the maturation of this application into a patent. However, the availability of these seeds is not to be construed as a license to practice this invention in contravention of rights granted under the authority of any government in accordance with its patent or breeder's rights laws.

The herbicide tolerance of PM-1 and/or PM-2 can be readily imparted to rape plants of the present invention such as D-98-49-176 (discussed hereafter) by cross-pollination followed by selection and the fixing of such trait in combination with the desired unusually low saturated fatty acid content by self-pollination and/or doubled haploidy.

The following Examples are presented as specific illustrations of the claimed invention. It should be understood, however, that the invention is not limited to the specific details set forth in the Examples.

EXAMPLE I

Seeds of the Topas variety of *Brassica napus* were selected as the starting material. This variety of canola is of the summer type and is suitable to produce an edible vegetable oil when grown in the north central region of the United States, the southern Alberta and Ontario regions of Canada, Sweden, and other areas where summer rape is adapted. The Topas variety was registered in 1987 by Svalof A B of Sweden. Planting seed for the Topas variety is available from Bonis & Company, Ltd., Lindsay, Ontario, Canada. A representative sample (i.e., 2.0 grams) of the mature seeds of the starting material was produced in a greenhouse at Georgetown, Ontario, Canada, and contained in the endogenous oil following crushing and extraction the fatty acids in the approximate concentrations indicated below in Table A based upon the total weight of the fatty acids present while using the gas liquid chromatography analysis technique previously described in the work of J. K. Daun et al., *J. Amer. Oil Chum. Soc.* 60:1751–1754 (1983) which is herein incorporated by reference:

TABLE A

| Fatty Acid | Number of Carbon Atoms Per Molecule | Number of Double Bonds Per Molecule | Weight Percent |
| --- | --- | --- | --- |
| Palmitic | 16 | 0 | 4.5 |
| Palmitoleic | 16 | 1 | 0.4 |
| Stearic | 18 | 0 | 1.1 |
| Oleic | 18 | 1 | 60.7 |
| Linoleic | 18 | 2 | 21.1 |
| Alpha-linolenic | 18 | 3 | 9.3 |
| Arachidic | 20 | 0 | 0.6 |
| Eicosenoic | 20 | 1 | 1.4 |
| Behenic | 22 | 0 | 0.4 |
| Erucic | 22 | 1 | non-detectable |

The glucosinolate content in the solid component following crushing and extraction of the oil was 9 micromoles per gram as determined by the gas liquid chromatography method of the Canadian Grain Commission.

Prior to chemical mutagenesis the seeds of the Topas variety of canola were stored under conditions so as to maintain good viability. More specifically, the seeds were stored in a cold storage room maintained at approximately 10° C. and 40 percent relative humidity.

Ten seed lots of the Topas variety each consisting of 1000 seeds were subjected to mutagenesis while employing a chemical mutagen. More specifically, each seed lot was treated with ethylnitrosourea. The ethylnitrosourea was present in dimethylsulfoxide solvent at a concentration of 9 mM. (millimoles). During the preparation of the ethylnitrosourea solution, 25 ml. of dimethylsulfoxide were added to one gram of ethylnitrosourea. The volume of ethylnitrosourea solution was brought to 50 ml. by adding 25 ml. of distilled water. The resulting solution was diluted further with 5 mM. (millimoles) of morpholinoethanesulfonic acid buffer at pH 5.5 to yield a 9 mM. (millimoles) concentration for use. Each seed lot was placed in a large petri dish and 30 ml. of the buffered ethylnitrosourea solution were added. The seeds next were incubated in the dark for 20 to 22 hours while at a temperature of approximately 20° C. The seeds next were rinsed three times and were planted in a soilless medium at a rate of 500 seeds per flat in a greenhouse at Georgetown, Ontario, Canada.

Approximately 25 percent of the seeds following the chemical mutagenesis treatment germinated to form M1 plants. The M1 plants were transplanted to pots in a greenhouse at the same location having a day temperature of approximately 25°±3° C. and a night temperature of approximately 18° C. Self-pollination was attempted and approximately 15 percent of these plants produced M2 seed.

The resulting M2 seed was harvested from individual plants by collecting pods from 3 to 4 lateral branches and was packaged. When the seed set was particularly poor, seeds were pooled from 20 to 40 racemes from up to 10 plants and were placed in a single package. A total of 111 packages of M2 seeds were harvested. Five whole seeds from each package were individually analyzed for fatty acid composition using the gas liquid chromatography analysis technique previously described. The fatty acid composition of the five single seed analyses were averaged and the results were used to identify those lines which formed an endogenous oil having a reduced saturated fatty acid content. A line designated F32 was selected which exhibited the lowest saturated fatty content of 4.97 percent by weight in the form of stearic and palmitic acids based upon the total fatty acid content.

M2 seeds from the F32 selection next were soaked in water and one halfseed (i.e., cotyledon) from each seed was carefully removed for the analysis of its fatty acid composition. Such halfseed analysis was carried out in accordance with the procedure of "Methods for Breeding for Oil Quality in Rape" by R. K. Downey and B. L. Harvey reported in the Canadian Journal of Plant Science, Vol. 43, pages 271 to 275 (1963). One hundred halfseeds were analyzed for oil content and of these 26 were selected having a saturated fatty acid content in the form of stearic and palmitic acids ranging from 3.74 to 4.5 percent by weight in the form of stearic and palmitic acids based upon the total fatty acid content. All of the 26 selections were planted in the greenhouse using the remaining halfseeds in an attempt to form plants. Only 13 of the M2 plant selections produced M3 seeds following self-pollination.

The halfseed procedure was next used to analyze and select M3 seeds on the basis of reduced fatty acid content in the oil. One line designated F32–38 was selected wherein 55 percent of the M3 seeds exhibited an endogenous saturated fatty acid content in the form of stearic and palmitic acids of less than 4 percent by weight. More specifically, the saturated fatty acid contents in the form of stearic and palmitic acids for these lower saturated fatty acid selections ranged from 3.43 to 3.97 percent by weight based upon the total fatty acid content. The M3 halfseed which exhibited the 3.43 percent value was then planted and produced an M3 plant designated F32-38-227. M4 seeds produced by this M3 plant possessed the following endogenous fatty acid concentrations in the oil following crushing and extraction as reported in Table B:

TABLE B

| Fatty Acid | Number of Carbon Atoms Per Molecule | Number of Double Bonds Per Molecule | Weight Percent |
| --- | --- | --- | --- |
| Palmitic | 16 | 0 | 2.51 |
| Palmitoleic | 16 | 1 | 0.24 |
| Stearic | 18 | 0 | 0.92 |
| Oleic | 18 | 1 | 65.47 |
| Linoleic | 18 | 2 | 18.39 |
| Alpha-linolenic | 18 | 3 | 9.95 |
| Arachidic | 20 | 0 | 0.33 |
| Eicosenoic | 20 | 1 | 1.71 |
| Behenic | 22 | 0 | 0.20 |
| Erucic | 22 | 1 | non-detectable |
| Lignoceric | 24 | 0 | 0.27 |

An M3 halfseed from a closely related line designated F32-38-172 which exhibited a fatty acid content in the oil of 3.7 percent by weight of stearic and palmitic acids based upon the total fatty acid content was planted in the greenhouse and a plant was produced which formed M4 seeds following self-pollination. The fatty acid composition of the F32-38 -172 seeds from the M4 generation was initially determined by the bulk analysis of 50 seeds and possessed the following endogenous fatty acid concentrations in the oil following crushing and extraction as reported in Table C:

TABLE C

| Fatty Acid | Number of Carbon Atoms Per Molecule | Number of Double Bonds Per Molecule | Weight Percent |
| --- | --- | --- | --- |
| Palmitic | 16 | 0 | 3.04 |
| Palmitoleic | 16 | 1 | 0.18 |
| Stearic | 18 | 0 | 1.19 |
| Oleic | 18 | 1 | 67.19 |
| Linoleic | 18 | 2 | 17.24 |
| Alpha-linolenic | 18 | 3 | 8.13 |
| Arachidic | 20 | 0 | 0.52 |
| Eicosenoic | 20 | 1 | 2.08 |
| Behenic | 22 | 0 | 0.35 |
| Erucic | 22 | 1 | non-detectable |
| Lignoceric | 24 | 0 | non-detectable |

When 118 seeds of F32-38-172 from the M4 generation were analyzed by the halfseed analysis previously described they were found to exhibit on a weight basis in the oil stearic acid contents which ranged from 0.68 to 2.22 percent, palmitic acid contents which ranged from 2.44 to 5.64 percent, alpha-linolenic acid contents which ranged from 5.65 to 18.85 percent by weight, and erucic acid contents which ranged from a non-detectable amount to 1.12 percent by weight based upon the total fatty acid content. The average stearic acid content was 1.06 percent by weight and the average palmitic acid content was 3.21 percent. The lowest combined stearic and palmitic contents in a single halfseed was 3.31 percent by weight and the highest combined stearic and palmitic acid contents was 7.07 percent by weight, with an average of 4.26 percent by weight being exhibited. In all instances the glucosinolate content in the solid component following crushing and extraction of the oil was less than 30 micromoles per gram as determined by the gas chromatography method of the Canadian Grain Commission.

Further selection was made within the F32-38-172 seeds to locate specific lines exhibiting even lower combined stearic and palmitic acid contents. More specifically, seeds and halfseeds were obtained from this plant line and were grown in a greenhouse in the manner hereinbefore described to provide plants of the M5 generation. The seed from each plant line was then analyzed by the bulk analysis of 50 seeds/plant to determine the saturated fatty acid content in those seeds. Seeds harvested from one plant designed F32-38-172-X possessed the following fatty acid content in the oil following crushing and extraction as reported in Table D:

TABLE D

| Fatty Acid | Number of Carbon Atoms Per Molecule | Number of Double Bonds Per Molecule | Weight Percent |
| --- | --- | --- | --- |
| Palmitic | 16 | 0 | 3.01 |
| Palmitoleic | 16 | 1 | 0.19 |
| Stearic | 18 | 0 | 0.80 |
| Oleic | 18 | 1 | 70.64 |
| Linoleic | 18 | 2 | 14.24 |
| Alpha-linolenic | 18 | 3 | 8.24 |
| Arachidic | 20 | 0 | 0.39 |
| Eicosenoic | 20 | 1 | 2.13 |
| Behenic | 22 | 0 | 0.27 |
| Erucic | 22 | 1 | non-detectable |
| Lignoceric | 24 | 0 | non-detectable |

Comparable M5 generation rapeseeds of the plant line designated F32-38-172-X have been deposited under the Budapest Treaty in the American Type Culture Collection, 12301 Parklawn Drive, Rockville, Md., 20852, U.S.A., on Jun. 27, 1989. This seed deposit has received Accession No. 40624, and will be made available upon the maturation of this application into a patent. However, the availability of these seeds is not to be construed as a license to practice this invention in contravention of rights granted under the authority of any government in accordance with its patent or breeder's rights laws.

Plant lines which form seeds exhibiting a further reduction in the saturated fatty acid content of the oil have been obtained upon further selection within the F32-38-172-X line. In particular, when the halfseed technique was applied to determine the saturated fatty acid content of individual seeds produced by F32-38-172-X, it was found that 23 percent of the 225 cotyledons analyzed exhibited a saturated fatty acid content lower than the 3.81 percent value revealed upon bulked seed analysis. One cotyledon in particular revealed in its oil a combined stearic and palmitic acid content of 3.34 percent by weight. A plant designated F32-38-172-X-24 was grown from this particular cotyledon and the seed formed thereon was determined by the bulk analysis of 50 seeds to possess a combined palmitic and stearic acid content in its oil of 3.66 percent by weight.

EXAMPLE II

Plant lines which form seeds exhibiting a reduced saturated fatty acid content have also been obtained through the use of the doubled haploid technology. In particular, a doubled haploid plant line was developed using as starting material the plant line F32-38-172-X produced as described hereinabove in Example I.

More specifically, young flower buds from upper racemes formed on the M5 plant line F32-38-172-X were macerated after surface sterilization to extract microspores therefrom in the manner described by Swanson et al in *Plant Cell Reports*, 6:94–97 (1987) which is herein incorporated by reference. Microspores isolated in this manner were then suspended in a modified Lichter microspore medium containing 13 percent sucrose but without potato extract and hormones, and incubated overnight at 30° C. The microspores were then recentrifuged and resuspended in a fresh microspore medium. Aliquots of the suspension (2.5 ml.) were plated individually at a rate of about 200,000 microspores per plate and the resulting plates were maintained at 30° C. With 12 to 14 days of incubation, approximately 160 embryos had formed. These embryos were then incubated in the dark at 25° C. on a gyratory shaker.

Plant regeneration was accomplished using the protocol described by Swanson et al in *Plant Cell Reports*, 7:83–87 (1988) which is herein incorporated by reference. Twenty-day old torpedo-shaped embryos were transferred to and maintained on hormone-free B5 medium supplemented with 0.45 percent agrose and 2 percent sucrose. Plantlets with true leaves which developed from the embryos were then planted directly into vermiculite and transferred to the greenhouse. Thirty-two plants were successfully regenerated following this microspore procedure.

The haploid regenerated plants were then exposed to the chromosome-doubling action of colchicine by maintaining the plantlet roots in a 0.2 percent solution of colchicine for about 6 hours. After rinsing the roots in water, the plantlets were repotted in compost and grown in the greenhouse until seeds formed following self-pollination. Seeds from 22 of the resulting doubled haploid plants were then examined for the content of the fatty acids in the endogenous seed oil. A range of saturated fatty acid levels was observed from 3.65 to 6.70 percent by weight in the form of stearic and palmitic acids. A plant line designed DH-SC6-8 was identified as the source of the 3.65 percent by weight saturated fatty acid composition. Twenty seeds formed thereon were bulked to analyze the overall endogenous fatty acid content of the oil. The results of the analysis are reported in Table E below:

TABLE E

| Fatty Acid | Number of Carbon Atoms Per Molecule | Number of Double Bonds Per Molecule | Weight Percent |
| --- | --- | --- | --- |
| Palmitic | 16 | 0 | 2.95 |
| Palmitoleic | 16 | 1 | 0.17 |
| Stearic | 18 | 0 | 0.70 |
| Oleic | 18 | 1 | 63.10 |
| Linoleic | 18 | 2 | 15.32 |
| Alpha-linolenic | 18 | 3 | 13.25 |
| Arachidic | 20 | 0 | 0.33 |
| Eicosenoic | 20 | 1 | 1.93 |
| Behenic | 22 | 0 | 0.25 |
| Erucic | 22 | 1 | non-detectable |
| Lignoceric | 24 | 0 | non-detectable |

Additional selection within the F32-38-172-X line using conventional techniques and/or additional mutagenesis in accordance with techniques heretofore described will result in the identification of plants which form seeds exhibiting a further reduction in the saturated fatty acid content of the oil in a subsequent generation in combination with the specified erucic acid content. Continued self-pollination and/or haploid production will result in the formation of plants which exhibit a substantially uniform phenotype. These plants can be preserved and multiplied using conventional techniques. Alternatively, a plant which following initial mutagenesis possesses the lowest stearic acid content can be crossed with a plant which following mutagenesis exhibits the lowest palmitic acid content, and appropriate selections made within the progeny.

EXAMPLE III

Seeds of the Glacier variety of Brassica napus were selected as the starting material. This variety of canola is of the winter type and is suitable to produce an edible vegetable oil when grown in southern portions of the United States, the southern portion of the Canadian province of Ontario, in Sweden, and in other countries. The Glacier variety is available commercially from Northern Sales Co. Ltd., Winnipeg, Ontario, Canada and typically produces an endogenous oil containing the following fatty acids in the approximate concentrations indicated below in Table F based upon the total weight of fatty acids present while using the gas liquid chromatography analysis technique previously described in the work of J. K. Daun et al., supra:

TABLE F

| Fatty Acid | Number of Carbon Atoms Per Molecule | Number of Double Bonds Per Molecule | Weight Percent |
| --- | --- | --- | --- |
| Palmitic | 16 | 0 | 4.89 |
| Palmitoleic | 16 | 1 | 0.34 |
| Stearic | 18 | 0 | 1.44 |
| Oleic | 18 | 1 | 59.66 |
| Linoleic | 18 | 2 | 19.36 |

TABLE F-continued

| Fatty Acid | Number of Carbon Atoms Per Molecule | Number of Double Bonds Per Molecule | Weight Percent |
| --- | --- | --- | --- |
| Alpha-linolenic | 18 | 3 | 11.50 |
| Arachidic | 20 | 0 | 0.55 |
| Eicosenoic | 20 | 1 | 1.36 |
| Behenic | 22 | 0 | 0.49 |
| Erucic | 22 | 1 | 0.16 |
| Lignoceric | 24 | 0 | 0.25 |

A representative sample (ten seed lots each consisting of 1000 seeds) of mature seeds of the Glacier variety was subjected to ethylnitrosourea (9 mM.) mutagenesis in substantially the same manner as is reported in Example I. The surviving M1 plants were vernalized and then transplanted to pots in a greenhouse having a day temperature of approximately 25°±3° C. and a night temperature of approximately 18° C. Following self-pollination, M2 seeds were harvested from each plant and halfseed screening was used to identify and select mutants with reduced saturated fatty acid content.

One M2 cotyledon sample designated Glacier D-98-49 was found to possess in its oil a combined palmitic and stearic acid content of 4.04 percent by weight. A plant was then grown from the remaining cotyledon and seed formed thereon was analyzed by the bulked seed approach. More specifically, analysis of a bulked 20 seed lot of the M3 seed obtained from the D-98-49 plant revealed a combined stearic and palmitic acid content in the oil of 4.34 percent by weight. To select further within this line for even lower saturated fatty acid content, 252 of the M3 seeds obtained therefrom were analyzed by the halfseed test. Of these seeds, 3 percent were found to possess a saturated fatty acid content below 3 percent by weight. One M3 selection, designated D-98-49-176 was found possess by halfseed analysis a saturated fatty acid content in its oil of 2.80 percent by weight in the form of stearic acid and palmitic acid.

Following growth of the D-98-49-176 plant, which displayed a morphology typical of the Glacier variety from which it was derived, a bulked sample of 50 mature M4 seeds harvested therefrom was analyzed for fatty acid composition in the oil and was found to have a combined stearic and palmitic acid content of 3.05 percent by weight.

Comparable rapeseeds of the M4 generation designated D-98-49-176 have been deposited under the Budapest Treaty in the American Type Culture Collection, 12301 Parklawn Drive, Rockville, Md., 20852, U.S.A., on Mar. 15, 1990. This seed deposit has received Accession No. 40773, and will be made available upon the maturation of this application into a patent. However, the availability of these seeds is not to be construed as a license to practice this invention in contravention of rights granted under the authority of any government in accordance with its patent or breeder's rights laws.

Further analysis of seed formed on D-98-49-176 has revealed that further reduction in the saturated fatty acid levels can be achieved. More particularly, halfseed analysis of 227 seeds harvested from this line has identified one cotyledon which exhibits a combined stearic and palmitic acid content in its oil of 2.59 percent by weight. This cotyledon has been designated D-98-49-176-193.

A detailed expression of the fatty acid compositions of the various selections (discussed above) leading to the genesis of the D-98-49-176 line together with that of the D-98-49-176-193 cotyledon are found in Tables G and H which follow:

TABLE G

| Fatty Acid | Number of Carbon Atoms Per Molecule | Number of Double Bonds Per Molecule | D-98-49 M2 Cotyledon | D-98-49 M3 Bulk Seed | D-98-49-176 M3 Cotyledon |
| --- | --- | --- | --- | --- | --- |
| Palmitic | 16 | 0 | 2.63 | 3.13 | 2.10 |
| Palmitoleic | 16 | 1 | 0.21 | 0.27 | 0.24 |
| Stearic | 18 | 0 | 1.41 | 1.21 | 0.70 |
| Oleic | 18 | 1 | 68.33 | 65.72 | 61.54 |
| Linoleic | 18 | 2 | 15.33 | 16.92 | 19.15 |
| Alpha-linolenic | 18 | 3 | 9.79 | 10.54 | 4.22 |
| Arachidic | 20 | 0 | 0.52 | 0.53 | 0.32 |
| Eicosenoic | 20 | 1 | 1.22 | 1.37 | 1.35 |
| Behenic | 22 | 0 | 0.34 | 0.31 | 0.38 |
| Erucic | 22 | 1 | non-detectable | non-detectable | non-detectable |
| Lignoceric | 24 | 0 | 0.23 | non-detectable | 0.17 |

TABLE H

| Fatty Acid | Number of Carbon Atoms Per Molecule | Number of Double Bonds Per Molecule | D-98-49-176 M4 Bulk Seed | D-98-49-176-193 M4 Cotyledon |
| --- | --- | --- | --- | --- |
| Palmitic | 16 | 0 | 2.24 | 2.01 |
| Palmitoleic | 16 | 1 | 0.24 | 0.19 |
| Stearic | 18 | 0 | 0.81 | 0.58 |
| Oleic | 18 | 1 | 62.15 | 62.35 |
| Linoleic | 18 | 2 | 20.25 | 18.21 |
| Alpha-linolenic | 18 | 3 | 12.09 | 14.37 |
| Arachidic | 20 | 0 | 0.39 | 0.30 |
| Eicosenoic | 20 | 1 | 1.50 | 1.72 |
| Behenic | 22 | 0 | 0.28 | 0.26 |
| Erucic | 22 | 1 | non-detectable | non-detectable |
| Lignoceric | 24 | 0 | 0.21 | non-detectable |

Further selection within the D-98-49-176 line using conventional techniques and/or additional mutagenesis in accordance with the techniques heretofore described will result in the identification of plants which form seeds exhibiting a further reduction in the saturated fatty acid content of the oil in subsequent generations, in combination with the specified erucic acid content. Continued self-pollination and/or haploid production will result in the formation of plants which exhibit a substantially uniform phenotype. These plants can be preserved and multiplied using conventional techniques. Alternatively, a plant which following initial mutagenesis possesses the lowest stearic acid content can be crossed with a plant which following mutagenesis exhibits the lowest palmitic acid content, and appropriate selections made within the progeny. Additionally, genetic means for herbicide tolerance can be introduced into the plants of the present invention which is derived from a suitable source, such as PM-1, PM-2, etc., as heretofore described.

Although the invention has been described with preferred embodiments, it is to be understood that variations and modifications may be resorted to as will be apparent to those skilled in the art. Such variations and modifications are to be considered within the purview and scope of the claims appended hereto.

We claim:

1. A mature rapeseed obtained from a *Brassica napus* rape plant capable of yielding an improved edible endogenous vegetable oil of reduced palmitic and stearic saturated fatty acid content, said rapeseed having an oil which exhibits following crushing and extraction of said rapeseed (1) an unusually low saturated fatty acid content of 2 to 4 percent by weight based on the sum of stearic and palmitic acids in relation to the total fatty acid content wherein said palmitic and stearic saturated fatty acid content is controlled by genetic means for the expression of such trait obtainable by mutagenesis, and (2) an erucic acid content of no more than 2 percent by weight based on the total fatty acid content.

2. A rapeseed according to claim 1 which is capable of yielding an improved edible endogenous vegetable oil which exhibits following crushing and extraction an unusually low palmitic and stearic saturated fatty acid content of 2.5 to 4 percent by weight based on the sum of stearic and palmitic acids in relation to the total fatty acid content.

3. A rapeseed according to claim 1 which is capable of yielding an improved edible endogenous vegetable oil having an unusually low palmitic and stearic saturated fatty acid content of 2 to 3.5 percent by weight based on the sum of stearic and palmitic acids in relation to the total fatty acid content.

4. A rapeseed according to claim 1 which is capable of yielding an improved edible endogenous vegetable oil which exhibits following crushing and extraction an unusually low palmitic and stearic saturated fatty acid content of 2.5 to 3.5 percent by weight based on the sum of stearic and palmitic acids in relation to the total fatty acid content.

5. A rapeseed according to claim 1 which is capable of yielding an improved edible endogenous vegetable oil having an unusually low palmitic and stearic saturated fatty acid content of 2 to less than 3 percent by weight based on the sum of stearic and palmitic acids in relation to the total fatty acid content.

6. A rapeseed according to claim 1 which is capable of yielding an improved edible endogenous vegetable oil which exhibits following crushing and extraction an erucic acid content of less than 0.1 percent by weight based on the total fatty acid content.

7. A rapeseed according to claim 1 which is capable of yielding an improved edible endogenous vegetable oil which exhibits following crushing and extraction an erucic acid content of less than 0.05 percent by weight based on the total fatty acid content.

8. A rapeseed according to claim 1 wherein said edible endogenous vegetable oil exhibits following crushing and extraction an alpha-linolenic acid content of approximately 8 to 15 percent by weight based upon the total fatty acid content.

9. A rapeseed according to claim 1 which additionally has a glucosinolate content in the solid component of less than 100 micromoles per gram following crushing and extraction of the oil.

10. A rapeseed according to claim 1 which has a glucosinolate content in the solid component of the oil of less than 30 micromoles per gram following crushing and extraction of the oil.

11. A rapeseed according to claim 1 wherein said rapeseed additionally possesses genetic means for the production of a rape plant which exhibits tolerance to a herbicide when applied at a rate which is capable of destroying rape plants which lack said genetic means.

12. A rapeseed according to claim 1 wherein said rapeseed additionally possesses genetic means for the production of a rape plant which exhibits tolerance to a sulfonylurea or imidazolinone herbicide when applied at a rate which is capable of destroying rape plants which lack said genetic means.

13. A rapeseed according to claim 1 wherein said rapeseed possesses genetic means present in at least one of PM-1 having ATCC Accession No. 40683 and PM-2 having ATCC Accession No. 40684 for the expression of tolerance to a herbicide when applied at a rate which is capable of destroying rape plants which lack said genetic means.

14. A rapeseed according to claim 1 wherein said reduced palmitic and stearic saturated fatty acid content of said improved vegetable oil is the result of a mutation induced by man and said mutation was isolated by selection.

15. A rapeseed according to claim 1 wherein said reduced palmitic and stearic saturated fatty acid content of said improved vegetable oil is the result of a mutation induced by man with the use of a technique selected from the group consisting of contact with a chemical mutagen, gamma irradiation, and a combination of the foregoing, in at least one earlier generation and said mutation was isolated by selection at the conclusion of such mutagenesis.

16. A rapeseed according to claim 1 wherein said rapeseed upon growing and self-pollination is true-breeding for said palmitic and stearic saturated fatty acid, and erucic acid contents.

17. A *Brassica napus* rape plant which upon self-pollination is capable of forming rapeseeds which yield an improved edible endogenous vegetable oil, said rapeseeds having an oil which exhibits following crushing and extraction of said rapeseeds (1) an unusually low palmitic and stearic saturated fatty acid content of 2 to 4 percent by weight based on the sum of stearic and palmitic acids in relation to the total fatty acid content wherein said saturated fatty acid content is controlled by genetic means for the expression of such trait obtainable by mutagenesis, and (2) an erucic acid content of no more than 2 percent by weight based on the total fatty acid content.

18. A rape plant according to claim 17 wherein said rapeseeds are capable of yielding an improved edible endogenous vegetable oil which exhibits following crushing and extraction an unusually low palmitic and stearic saturated fatty acid content of 2.5 to 4 percent by weight based on the sum of stearic and palmitic acids in relation to the total fatty acid content.

19. A rape plant according to claim 17 wherein said rapeseeds are capable of yielding an improved edible endogenous vegetable oil which exhibits following crushing and extraction an unusually low palmitic and stearic saturated fatty acid content of 2 to 3.5 percent by weight based on the sum of stearic and palmitic acids in relation to the total fatty acid content.

20. A rape plant according to claim 17 wherein said rapeseeds are capable of yielding an improved edible endogenous vegetable oil which exhibits following crushing and extraction an unusually low palmitic and stearic saturated fatty acid content of 2.5 to 3.5 percent by weight based on the sum of stearic and palmitic acids in relation to the total fatty acid content.

21. A rape plant according to claim 17 wherein said rapeseeds are capable of yielding an improved edible endogenous vegetable oil which exhibits following crushing and extraction an unusually low palmitic and stearic saturated fatty acid content of 2 to less than 3 percent by weight based on the sum of stearic and palmitic acids in relation to the total fatty acid content.

22. A rape plant according to claim 17 wherein said rapeseeds yield an improved edible endogenous vegetable oil which exhibits following crushing and extraction an erucic acid content of less than 0.1 percent by weight based upon the total fatty acid content.

23. A rape plant according to claim 17 wherein said rapeseeds yield an improved edible endogenous vegetable oil which exhibits following crushing and extraction an erucic acid content of less than 0.05 percent by weight based upon the total fatty acid content.

24. A rape plant according to claim 17 wherein said rapeseeds yield an improved edible endogenous vegetable oil which exhibits following crushing and extraction an alpha-linolenic acid content of approximately 8 to 15 percent by weight based upon the total fatty acid content.

25. A rape plant according to claim 17 wherein said rapeseeds have a glucosinolate content in the solid component of said rapeseeds of less than 100 micromoles per gram following crushing and extraction of the oil.

26. A rape plant according to claim 17 wherein said rapeseeds additionally have a glucosinolate content in the solid component of said rapeseeds of less than 30 micromoles per gram following crushing and extraction of the oil.

27. A rape plant according to claim 17 which additionally possesses genetic means for tolerance to a herbicide when applied at a rate which is capable of destroying rape plants which lack said genetic means.

28. A rape plant according to claim 17 which additionally possesses genetic means for tolerance to a sulfonylurea or imidazolinone herbicide when applied at a rate which is capable of destroying rape plants which lack said genetic means.

29. A rape plant according to claim 17 wherein said rape plant possesses genetic means present in at least one of PM-1 having ATCC Accession No. 40683 and PM-2 having ATCC Accession No. 40684 for the production of rape plants which exhibit tolerance to a herbicide when applied at a rate which is capable of destroying rape plants which lack said genetic means.

30. A rape plant according to claim 17 wherein said reduced fatty acid content of said rapeseeds is the result of a mutation induced by man and said mutation was isolated by selection.

31. A rape plant according to claim 17 wherein said reduced palmitic and stearic fatty acid content of said rapeseeds is the result of a mutation which was induced by man with the use of a technique selected from the group consisting of contact with a chemical mutagen, gamma irradiation, and a combination of the foregoing, in at least one earlier generation and said mutation was isolated by selection at the conclusion of such mutagenesis.

32. A rapeseed according to claim 1 which was produced in the field under conventional rape growing conditions.

33. A rape plant according to claim 17 which was produced in the field under conventional rape growing conditions.

* * * * *